United States Patent [19]

Ohno et al.

[11] Patent Number: 5,714,648
[45] Date of Patent: Feb. 3, 1998

[54] PROCESS FOR PRODUCING TETRAFLUOROMETHANE

[75] Inventors: Hiromoto Ohno; Tetsuo Nakajo; Tatsuharu Arai; Toshio Ohi, all of Kanagawa, Japan

[73] Assignee: Showa Denko K.K., Tokyo, Japan

[21] Appl. No.: 630,532

[22] Filed: Apr. 10, 1996

[30] Foreign Application Priority Data

Mar. 8, 1996 [JP] Japan ............................. 8-51932

[51] Int. Cl.$^6$ ............................................. C07C 19/08
[52] U.S. Cl. ............................................. 570/123
[58] Field of Search ............................................. 570/123

[56] References Cited

FOREIGN PATENT DOCUMENTS 1116920  6/1968  United Kingdom ............... 570/123

OTHER PUBLICATIONS

JACS PP. 3302–3303 vol. 62 (1940) Hadley et al.

Primary Examiner—Alan Siegel
Attorney, Agent, or Firm—Sughrue, Mion, Zinn, Macpeak & Seas, PLLC

[57] ABSTRACT

A process for producing tetrafluoromethane which comprises reacting a hydrofluorocarbon containing one carbon atom in the molecule with fluorine gas at an elevated temperature in a vapor phase in the presence of a diluent gas.

12 Claims, No Drawings

PROCESS FOR PRODUCING TETRAFLUOROMETHANE

FIELD OF THE INVENTION

The present invention relates to a process for producing tetrafluoromethane by reacting a hydrofluorocarbon containing one carbon atom in the molecule with fluorine gas at an elevated temperature in a vapor phase in the presence of a diluent gas.

BACKGROUND OF THE INVENTION

Tetrafluoromethane (hereinafter abbreviated as "FC-14" or "$CF_4$") is used, for example, for the dry etching of semiconductors.

With respect to the production of FC-14, various methods have hitherto been proposed. Examples thereof include a method comprising reacting chlorotrifluoroethane ($CClF_3$) with HF in the presence of a catalyst (JP-B-62-10211; the term "JP-B" as used herein means an "examined Japanese patent publication"); a method comprising reacting dichlorodifluoromethane ($CClF_2F_2$) with HF in the presence of a catalyst (JP-B-42-3004); a method comprising reacting carbon tetrachloride ($CCl_4$) with HF (JP-B-43-10601); a method comprising reacting trifluoromethane ($CHF_3$) with $F_2$ (GB-1116920 (1968)); a method comprising reacting carbon (C) with $F_2$ in $BrF_3$ or $IF_5$ (JP-A-58-162536; the term "JP-A" as used herein means an "unexamined published Japanese patent application"); and a method comprising pyrolyzing tetrafluoroethylene ($CF_2=CF_2$) and $CO_2$ at a high temperature (U.S. Pat. No. 4,365,102 (1982)).

The reactions in which HF is used not only yield a large amount of hydrochloric acid as a by-product, but necessitate a high temperature. Further, the method in which tetrafluoroethylene and $CO_2$ are pyrolyzed at a high temperature not only necessitates a high pyrolysis temperature of 1,100° to 1,300° C., but results in a low yield.

The direct fluorination method using fluorine gas ($F_2$) has drawbacks that since fluorine gas, which is extremely reactive, is used, there is a danger of explosion of the organic compound as a substrate and fluorine gas and there is a danger of corrosion, etc. In addition, there are a danger of side reactions including the cleavage and polymerization of C—C bonds due to heat generation and a fear of an abrupt reaction or explosion due to the formation and deposition of carbon, etc.

For example, in the case of synthesizing a perfluoro compound from a linear hydrocarbon and fluorine gas by the direct fluorination method, the reaction is accompanied by an exceedingly large quantity of heat as shown in schemes (1) and (2).

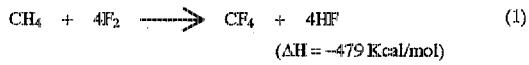

$$CH_4 + 4F_2 \longrightarrow CF_4 + 4HF \quad (1)$$
$$(\Delta H = -479 \text{ Kcal/mol})$$

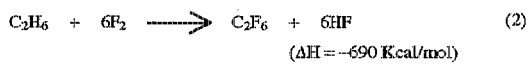

$$C_2H_6 + 6F_2 \longrightarrow C_2F_6 + 6HF \quad (2)$$
$$(\Delta H = -690 \text{ Kcal/mol})$$

The reaction shown by scheme (1), in which methane is used as a starting material, needs 4 mol of fluorine per mol of methane, while the reaction shown by scheme (2), in which ethane is used as a starting material, needs 6 mol of fluorine gas per mol of ethane. Thus, the quantity of heat of reaction is proportional to the number of moles of fluorine; the larger the fluorine amount, the larger the quantity of heat of reaction. The increased heat of reaction tends to cause the cleavage of C—C bonds, explosion, etc., and results in a reduced yield, thus posing problems concerning industrial production and operation.

Techniques used for inhibiting the abrupt generation of heat of reaction in the direct fluorination method include: to dilute fluorine with an inert gas (e.g., nitrogen or helium); to dissolve the organic compound as a substrate beforehand into a solvent inert to fluorine to prepare a low-concentration solution; and to conduct the reaction in a low-temperature region. For the reaction conducted in a vapor phase, a devised apparatus such as, e.g., a jet reactor has been proposed so that fluorine comes into contact with the organic compound as a substrate little by little.

The prior art methods for reacting organic compounds with fluorine gas as described hereinabove have the measures described above. For example, in the reaction proposed in GB-1116920, a measure for contacting fluorine gas with trifluoroethane little by little in the absence of a diluent gay is taken. Further, in the reaction proposed in JP-A-58-162536, the organic compound as a substrate is dissolved in a solvent inert to fluorine to prepare a low-concentration solution. However, such prior art techniques have much room for improvement in safety and cost.

SUMMARY OF THE INVENTION

The present invention has been achieved in order to eliminate the problems described above and to accomplish the subject described above. Accordingly, an object of the present invention is to provide a process by which FC-14 can be safely and efficiently produced at low cost by the direct fluorination method using an organic compound as a substrate and fluorine gas.

Other objects and effects of the present invention will be apparent from the following description.

The present invention provides a process for producing tetrafluoromethane which comprises reacting a hydrofluorocarbon containing one carbon atom in the molecule with fluorine gas at an elevated temperature in a vapor phase in the presence of a diluent gas.

DETAILED DESCRIPTION OF THE INVENTION

The diluent gas desirably comprises at least one of tetrafluoromethane, hexafluoroethane, octafluoropropane, and hydrogen fluoride, and is preferably rich in hydrogen fluoride (the hydrogen fluoride content thereof being preferably 50% or higher based on the total amount of the diluent gas).

The organic compound used as a substrate is a hydrofluorocarbon (HFC) containing one carbon atom in the molecule. Specifically, the substrate comprises at least one compound selected from fluoromethane ($CH_3F$), difluoromethane ($CH_2F_2$), and trifluoromethane ($CHF_3$), and is preferably difluoromethane and/or trifluoromethane.

In carrying out the reaction, the concentration of the hydrofluorocarbon containing one carbon atom in the molecule as measured at the reactor inlet is preferably regulated to 8 mol % or lower. The reaction is conducted at an elevated temperature, which is preferably in the range of from 200° to 550° C. The reaction is preferably performed at a pressure of from 0 to 3 MPa.

The process for producing FC-14 according to the present invention is explained below in detail.

The organic compound used as a starting material in the present invention, which is a hydrofluorocarbon containing one carbon atom in the molecule, is represented by formula (3).

$CH_xF_y$ (3)

In formula (3), x is an integer of $1 \leq x \leq 3$ and y is an integer of $1 \leq y \leq 3$, provided that $x+y=4$. Examples of this compound are fluoromethane, difluoromethane, and trifluoromethane. These starting materials may be used either alone or as a mixture of two or more thereof.

As stated hereinabove, the reaction of an organic compound with fluorine gas is accompanied by an exceedingly large quantity of heat, and the quantity of heat of reaction is proportional to the number of moles of fluorine, i.e., the larger the fluorine amount, the larger the quantity of heat of reaction. Because of this, the smaller the number of H atoms which should be replaced by F atoms, the easier the control of the heat of reaction and the smaller the use amount of fluorine, which is expensive. Consequently, desirable starting materials among the aforementioned hydrofluorocarbons are the compounds containing a larger number of fluorine atoms in the molecule, specifically, difluoromethane and/or trifluoromethane.

Difluoromethane is being industrially produced as a substitute for hydrochlorofluorocarbons (HCFC), and while trifluoromethane is also being industrially produced as a refrigerant. Both are hence easily available, and commercial products thereof have a purity as high as 99.9% or higher.

In the case of the production of FC-14 from these compounds and fluorine gas, the heat of reaction is as shown in schemes (4) and (5).

$$CH_2F_2 + 2F_2 \longrightarrow CF_4 + 2HF \quad (4)$$
$$(\Delta H = -259 \text{ Kcal/mol})$$

$$CHF_3 + F_2 \longrightarrow CF_4 + HF \quad (5)$$
$$(\Delta H = -120 \text{ Kcal/mol})$$

Thus, by using difluoromethane or trifluoromethane as a starting material, the quantity of heat of reaction can be as small as about from ½ to ¼ of those in the proportion of FC-14 from hydrocarbon compounds and fluorine gas, and that the use amount of fluorine is also small.

Another important point concerning the hydrofluorocarbon used as a starting material is impurities contained therein. For example, inclusion of chlorine compounds such as, e.g., chlorofluoromethane ($CH_2ClF$), chlorotrifluoromethane ($CClF_3$), and chlorodifluoromethane ($CHClF_2$) is not preferred in that they react with fluorine to yield by-products such as chlorine fluoride and chlorine. Therefore, the hydrofluorocarbon used as a starting material is desirably free from these chlorine compounds.

The reaction of the hydrofluorocarbon described above with fluorine gas is conducted at an elevated temperature in the presence of a diluent gas.

Although an inert gas such as nitrogen, helium, or argon is generally employed as a diluent gas, this method is not always advantageous in energy cost in view of the necessity of separation of the inert gas from the objective compound and purification thereof. In a preferred embodiment of the present invention, a gas comprising at least one of tetrafluoromethane (boiling point: −127.9° C.), hexafluoroethane (boiling point: −78.5° C.), octafluoropropane (boiling point: −37.7° C.), and hydrogen fluoride (boiling point: 20° C.) is used as the diluent gas. These diluent compounds not only have the effect of inhibiting combustion, explosion, etc., but also are advantageous in energy cost for separation and purification because they have a higher boiling point than helium (boiling point: −268.9° C.) and other diluent gases. It is especially preferred to use a diluent gas rich in hydrogen fluoride (the hydrogen fluoride content thereof being preferably 50% or higher based on the total amount of the diluent gas).

For example, the reaction between 1 mol of difluoromethane and 2 mol of fluorine yields 1 mol of FC-14 and 2 mol of hydrogen fluoride, as shown by scheme (4). Since the difference in boiling point between the objective compound, i.e., FC-14, and the by-product, i.e., hydrogen fluoride, is about 150° C., a gas rich in hydrogen fluoride can be obtained by a simple method such as, e.g., partial condensation. Use of this gas as a diluent gas is economical. Alternatively, hydrogen fluoride may be newly added as a diluent gas. In the direct fluorination method in which fluorine gas is used, carbon formation, deposition, etc. occur during the long-term reaction as stated hereinabove. Although the carbon formation, deposition, etc. may cause a danger of an abrupt reaction with fluorine gas or explosion, the use of hydrogen fluoride as a diluent gas is effective in inhibiting the formation and deposition of carbon. The term "rich in hydrogen fluoride" means "containing hydrogen fluoride as a major component."

The reaction of a reaction substrate with fluorine gas is conducted in the presence of a diluent gas. Before being introduced into a reactor, either or both of the reaction substrate and fluorine gas are generally diluted with the diluent gas. From the standpoint of safety, both the reaction substrate and the fluorine gas are preferably diluted with the diluent gas in a sufficiently low concentration.

Reaction temperature is among the conditions which should be taken in account in order to efficiently carry out the reaction of the starting material, i.e., a hydrofluorocarbon of the kind described above, with fluorine gas in the presence of a diluent gas such as those described above. The optimum range of reaction temperature varies depending on the contact time and the kind of the hydrofluorocarbon as a starting material.

For example, in the case where the reaction of difluoromethane with fluorine is conducted using a long contact time (15 seconds), the reaction begins at a reaction temperature of about 50° C. and the conversion reaches about 100% at a temperature of about 250° C. An elevated reaction temperature is used, preferably in the range of from 200° to 55° C. Reaction temperatures lower than 200° C. are not preferred in that the conversion of the hydrofluorocarbon is low. Reaction temperatures exceeding 550° C. are undesirable in, for example, that polymerization, carbon deposition, etc. occur to result in a reduced yield, and that there are problems such as reactor corrosion and an increased energy cost.

Although the contact time is not particularly limited, it is in the range of, for example, from 0.1 to 120 seconds. In general, however, the contact time is desirably from 1 to 30 seconds, preferably from 3 to 20 seconds, since longer contact times necessitate a larger reactor and are hence uneconomical. It is preferred to well mix the reaction substrate with the fluorine gas.

As stated hereinabove, in the direct fluorination method in which fluorine gas is used, there is the danger that the organic compound as a substrate (in particular a compound containing hydrogen) may burn or explode upon exposure to fluorine, because fluorine is extremely reactive.

In the reaction of the present invention, it is important that since a hydrofluorocarbon, containing hydrogen, is used as the organic compound substrate, the explosion of the hydrofluorocarbon and fluorine should be prevented. For preventing explosion, the mixed gas should be regulated so as to have a composition outside the explosion range therefor. As a result of investigations made by the present inventors on the explosion ranges for mixtures of hydrofluorocarbons with fluorine gas, the lower limit of the explosion range for trifluoromethane was found to be a concentration of about 8 mol %. It is preferred that the concentration of the hydrofluorocarbons of the present invention as measured at the reactor inlet be regulated so as to be within the respective safety ranges therefor.

The molar ratio of the fluorine gas to the hydrofluorocarbon both fed to the reaction system is preferably from 0.5 to 5.0, more preferably from 1.0 to 3.0. If the molar proportion of the fluorine gas fed is below 0.5, the reaction does not proceed efficiently. Molar proportions thereof exceeding 5.0 are uneconomical in that fluorine gas is fed in excess and this necessitates, for example, an apparatus for the recovery thereof.

In carrying out the reaction, the reaction pressure is also important from the standpoint of preventing dangers such as explosion. In general, the higher the pressure, the wider the explosion range. Consequently, the reaction is conducted desirably at a lower pressure, preferably in the range of from 0 to 3 MPa.

The reactor is preferably made of a material having resistance to corrosive gases. Examples of the material include nickel, Inconel, and Monel.

The following are Examples of the present invention, but the invention should not be construed as being limited thereto.

The starting materials used in the following reactions are shown below first.

(Difluoromethane)

Difluoromethane ($CH_2F_2$) Ecoloace 32 (trade name, manufactured by Showa Denko K.K., Japan), which is currently being supplied as a substitute for HCFC-22 ($CHClF_2$), was used. It had a purity of 99.99% or higher, and contained 1,1,1-trifluoroethane ($CF_3CH_3$) and fluoromethane ($CH_3F$) as impurities. Almost no chlorine compound was detected therein.

(Trifluoromethane)

Trifluoromethane ($CHF_3$) Ecoloace 23, which is currently being supplied as a refrigerant, was used. It had a purity of 99.95% or higher, and contained chlorine compounds including chlorodifluoromethane ($CHClF_2$) and chlorotrifluoromethane ($CClF_3$) as impurities.

EXAMPLE 1

An Inconel 600 reactor having an inner diameter of 20.6 mm and a length of 500 mm (electrical heating type; the reactor had undergone a passivation treatment with fluorine gas at 600° C.) was heated to 280° C. while introducing nitrogen gas as a diluent gas thereinto at a rate of 30 NL/h. Subsequently, hydrogen fluoride was introduced thereinto as a diluent gas at a rate of 50 NL/h. The flow of the diluent gas was divided into two, to one of which was added difluoromethane as a hydrofluorocarbon at a rate of 1.8 NL/h. Thereafter, fluorine gas was fed by adding the same to the other of the divided diluent gas flows at a rate of 3.9 NL/h to conduct a reaction. The concentration of the hydrofluorocarbon as measured at the reactor inlet was 2.1 mol %, and the reaction temperature was 280° C.

Three hours after, the gaseous mixture resulting from the reaction was treated with aqueous potassium hydroxide solution and aqueous potassium iodide solution to remove the hydrogen fluoride and the unreacted fluorine gas. The residual gas was analyzed for composition by gas chromatography. As a result, the gas composition (vol %) was found to be as follows.

| | |
|---|---|
| $CF_4$ | 99.04% |
| $C_2F_6$ | 0.03% |
| $CH_2F_2$ | trace |
| Others | 0.93% |

EXAMPLES 2 AND 3

Reaction was carried out under the same conditions as in Example 1, except that the reaction temperature was changed. The reaction temperatures used and the results obtained are shown in Table 1.

TABLE 1

| Example | Reaction temperature (°C.) | Composition (vol%) | | | |
|---|---|---|---|---|---|
| | | FC-14 | FC-116 | HFC-32 | Others |
| 2 | 200 | 98.04 | trace | 1.08 | 0.88 |
| 3 | 400 | 98.56 | 0.46 | — | 0.98 |

In the table, FC-14 means $CF_4$, FC-116 means $C_2F_6$, HFC-32 means $CH_2F_2$, and Others consisted mainly of $CO_2$.

The results show that FC-14, the objective compound, was obtained in good yield. At the higher temperature, however, formation of a $C_3$ perfluoro compound was observed, which was yielded by polymerization, etc.

EXAMPLES 4 TO 8

Using the same reactor as in Example 1, reaction was carried out in the same manner as in Example 1, except that trifluoromethane as a hydrofluorocarbon and fluorine gas were fed at rates of 3.0 NL/h and 3.5 NL/h, respectively, and hydrogen fluoride and nitrogen gas were introduced as diluent gases at rates of 50 NL/h and 30 NL/h, respectively, and that the reaction temperature was varied. The reaction products thus obtained were analyzed in the same manner as in Example 1. The reaction temperatures used and the results obtained are shown in Table 2.

TABLE 2

| Example | Reaction temperature (°C.) | Composition (vol%) | | | |
|---|---|---|---|---|---|
| | | FC-14 | FC-116 | HFC-23 | Others |
| 4 | 200 | 7.36 | — | 91.88 | 0.76 |
| 5 | 300 | 84.40 | — | 14.76 | 0.84 |
| 6 | 400 | 98.89 | 0.19 | — | 0.92 |
| 7 | 500 | 98.62 | 0.32 | — | 1.06 |
| 8 | 600 | 96.04 | 1.08 | — | 2.88 |

In the table, HFC-23 means $CHF_3$. The results show that although trifluoromethane was less reactive in a low-temperature region than difluoromethane, it gave FC-14, the objective compound, in good yield. However, due to the chlorine compounds contained in the trifluoromethane used as a starting material, chlorine and chlorine fluoride were detected in Examples 7 and 8.

EXAMPLE 9

Using the same reactor as in Example 1, reaction was carried out in the same manner as in Example 1, except that trifluoromethane as a hydrofluorocarbon and fluorine gas were fed at rates of 3.0 NL/h and 3.5 NL/h, respectively, and hydrogen fluoride and hexafluoromethane were introduced at rates of 60 NL/h and 20 NL/h, respectively, and that the reaction temperature was changed to 450° C. The reaction product thus obtained was analyzed in the same manner as in Example 1. The results (vol %) obtained are shown below.

| | |
|---|---|
| $CF_4$ | 98.04% |
| $C_2F_6$ | 0.88% |
| $CHF_3$ | — |
| Others | 1.08% |

The reaction was continuously performed for 25 days under the conditions described above, and the gas collected at the reactor outlet at the 25th day was analyzed for composition. The results thus obtained were almost the same as the above. Thereafter, the reaction was terminated, and the reactor was cooled to room temperature while introducing nitrogen gas thereinto. The inner surface of the reactor was then examined with a fiber scope (endoscope). As a result, no deposit of carbon or another substance was observed.

According to the process of the present invention, FC-14 can be industrially and safely produced in high yield by reacting a hydrofluorocarbon containing one carbon atom in the molecule with fluorine gas in the presence of a diluent gas.

While the invention has been described in detail and with reference to specific embodiments thereof, it will be apparent to one skilled in the art that various changes and modifications can be made therein without departing from the spirit and scope thereof.

We claim:

1. A process for producing tetrafluoromethane which comprises reacting a hydrofluorocarbon containing one carbon atom in the molecule with fluorine gas in a reactor at an elevated temperature in a vapor phase in the presence of an added diluent gas comprising a gas selected from the group consisting of tetrafluoromethane, hexafluoroethane, octafluoropropane and hydrogen fluoride, said diluent gas being present in a sufficient quantity to dilute said hydrofluorocarbon below an explosive concentration range.

2. The process as claimed in claim 1, wherein the diluent gas is rich in hydrogen fluoride.

3. The process as claimed in claim 1, wherein the reaction is conducted at a temperature of from 200° to 550° C.

4. The process as claimed in claim 1, wherein the concentration of the hydrofluorocarbon containing one carbon atom in the molecule as measured at the reactor inlet is 8 mol % or lower.

5. The process as claimed in claim 1, wherein the hydrofluorocarbon containing one carbon atom in the molecule comprises at least one of fluoromethane, difluoromethane, and trifluoromethane.

6. The process as claimed in claim 1, wherein the hydrofluorocarbon containing one carbon atom in the molecule is difluoromethane and/or trifluoromethane.

7. The process as claimed in claim 1, wherein the reaction is conducted at a pressure of from 0 to 3 MPa.

8. The process according to claim 1, wherein an inlet of the concentration of said hydrofluorocarbon as measured at a reactor is approximately 2.1 mol %.

9. The process according to claim 1, wherein molar ratio of said fluorine gas to said hydrofluorocarbon is between 0.5 and 5.0.

10. The process according to claim 9, wherein the molar ratio is between 1.0 and 3.0.

11. The process according to claim 1, wherein said diluent gas comprises hydrogen fluoride.

12. The process according to claim 11, wherein said hydrogen fluoride constitutes 50% or greater of the total amount of said diluent gas.

* * * * *